United States Patent [19]

Lindstrom

[11] Patent Number: 4,930,510

[45] Date of Patent: * Jun. 5, 1990

[54] PARAMETERIZATION FOR CT BLOOD FLOW MAPPING WITH XENON GAS ENHANCEMENT

[75] Inventor: Walter W. Lindstrom, Shaker Hts., Ohio

[73] Assignee: Picker International, Inc., Highland Hts., Ohio

[*] Notice: The portion of the term of this patent subsequent to Dec. 27, 2005 has been disclaimed.

[21] Appl. No.: 275,785

[22] Filed: Nov. 23, 1988

Related U.S. Application Data

[63] Continuation-in-part of Ser. No. 933,781, Nov. 24, 1986, Pat. No. 4,793,357.

[51] Int. Cl.$^5$ .............................................. A61B 6/00
[52] U.S. Cl. .................................. 128/654; 128/659; 128/719
[58] Field of Search ............... 128/653, 654, 659, 719, 128/730; 250/303, 380

[56] References Cited

U.S. PATENT DOCUMENTS

| | | | |
|---|---|---|---|
| 3,769,966 | 11/1973 | Youdin et al. | 128/654 |
| 4,535,780 | 8/1985 | Gur et al. | 128/659 |
| 4,718,432 | 1/1988 | Kimura et al. | 128/654 |
| 4,793,357 | 12/1988 | Lindstrom | 128/654 |

OTHER PUBLICATIONS

"Progress in Cerebrovascular Disease" by Gur, et al., Stroke, vol. 13, No. 6, 1982, pp. 750-758.
"Regional Cerebral Blood Flow Measurement . . ." by Kishore, et al., Journal of Computer Assisted Tomography, Aug. 1984, 619-630.

Primary Examiner—Ruth S. Smith
Attorney, Agent, or Firm—Fay, Sharpe, Beall, Fagan, Minnich & McKee

[57] ABSTRACT

A xenon gas system (B) introduces xenon gas into a patient's blood. The xenon concentration in the patient's blood is monitored (26) periodically as the concentration builds toward a saturation level (32). The absorption data is divided into at least three curved segments (32, 34, 36) each of which are approximated by a curve segment to determine absorption curve characteristics. The amplitude of the saturation curve segment is determined as first characteristic; the slope of the second curve segment is a second characteristic; and an end amplitude and time constant of an exponential third curve segment provide third and fourth characteristics indicative of blood xenon absorption. A CT scanner (A) generates a plurality of time displaced image representations, each of which is subtracted (52) from a reference image (30) to determine difference image representations. Each image representation includes a plurality of pixels that correspond to subregions of a region of interest within the patient. A look-up table (60) is addressed by the absorption curve characteristics and corresponding pixel values to retrieve corresponding partition coefficient, blood flow, and fit or confidence values for each pixel. A video display (76) displays images indicative of the partition coefficient, blood flow rate, or confidence value of the imaged pixels.

18 Claims, 3 Drawing Sheets

PARAMETERIZATION FOR CT BLOOD FLOW MAPPING WITH XENON GAS ENHANCEMENT

This application is a continuation-in-part of U.S. application Ser. No. 933,781, filed Nov. 24, 1986, now U.S. Pat. No. 4,793,357.

BACKGROUND OF THE INVENTION

The present invention relates to the art of medical diagnostics. It finds particular application in conjunction with CT blood flow mapping of the brain and will be described with particular reference thereto. However, it is to be appreciated that the present invention will also find utility in conjunction with other imaging modalities, such as digital x-ray, magnetic resonance, radiation and position emission, ultrasound, and the like. The present invention is further applicable in imaging other regions of human and veterinary patients, inanimate objects, and other subjects.

In the brain, blood reaches the tissue in two modes—directly through the arteries and indirectly through other tissue. In normal, healthy brain tissue, blood reaches gray matter at 40 to 100 milliliters per 100 milliliters per minute. Gray matter tissue which receives less than 30 milliliters per 100 milliliters per minute is not adequately fed for proper functioning and may suffer irreparable damage. In white matter, cerebral blood flows are typically about one third of those for gray matter with flows under about 10 milliliters per 100 milliliters per minute being considered inadequate. The early detection of brain regions with subnormal blood flows enables corrective action to be taken before the affected tissue is irreversibly damaged.

One of the most common causes of insufficient feeding of the tissue is a blockage in the arterial blood flow. In the past, iodine has been utilized as an enhancement agent injected into the blood to facilitate the location of arterial blockages. However, brain tissue membrane blocks the iodine enhancement agent from permeating the tissue area. Because iodine is unable to pass from the blood into the tissue, iodine is only able to enhance images of blood in arteries, capillaries, and veins. Iodine is therefore unable to enhance the representations of the actual profusion of blood into the tissues.

Unlike iodine, xenon passes freely from the blood into the brain tissue. Thus, utilizing xenon gas as an enhancement agent facilitates the imaging and measurement of blood profusion into the tissue. As the concentration of xenon gas in the patient's blood rises, the concentration of xenon gas in the brain tissue also increases, asymptotically approaching equilibrium concentration. The rate of increase of gas concentration in the tissue is indicative of the blood flow rate. The equilibrium concentration, which is asymptotically approached is indicative of a partition coefficient $\lambda$. The partition coefficient, which is different for different kinds of tissue, is defined as the ratio of the quantity of xenon in each unit volume or voxel of tissue to the quantity of xenon per like volume in blood. For gray matter, the partition coefficient is typically about 0.9 and for white matter is typically about 1.3. Partition coefficients which differ significantly from these values are indicative of sick or dying tissue.

The xenon concentration in the tissue of the unit volume cell or voxel at a time t is described by the formula known as the Kety equation:

$$C(t) = f \int_O^T C_a(w) e^{-K(t-w)} dw, \qquad (1)$$

where C is tissue xenon concentration, $C_a$ is the blood xenon concentration, K is the tissue clearance or build-up rate, and f is the flow rate. The partition coefficient $\lambda$ is related to the flow rate and the clearance or build-up rate by the equation:

$$f = \lambda K \qquad (2),$$

where $\lambda$ is the tissue-blood partition coefficient.

The blood xenon concentration is readily monitorable. The tissue xenon concentration for a tissue in a given voxel can be calculated from the CT number or value of the pixel of a CT image corresponding to the given voxel. By taking several CT images at different times, with the blood xenon concentration known for times preceding each image, one can theoretically solve the Kety equation to determine the partition coefficient and blood flow for the tissue voxel corresponding to each pixel. Typically, three to six images have been taken. More particularly, the CT numbers or values from the corresponding pixels of each of the three to six images have been iteratively fit to the "best" flow f and partition coefficient which, with the "known" $C_a(w)$, allowed comparative C(t) to be calculated using any of various conventional curve fitting techniques.

Of course, $C_a(w)$ is not a directly measured value. Rather, it is approximated by making a best fit match of the data points to a single exponential curve. See for example Gur, et al., *Stroke*, Vol. 13, No. 6, Nov.-Dec. 1982, pp. 750–758. One major advantage of using the single exponential approximation is that it is readily able to be integrated when performing the calculation of Equation (1). Because the single exponential curve in many instances did not fit the generated data, it was proposed to use a dual-exponential. See for example Kishore, et al., *JCAT*, Vol. 8, No. 4, pp. 619–630 (Aug. 1984).

One of the drawbacks to the prior art exponential curve fitting techniques is that experimental data have not fit an exponential curve well for all patients. Those patients which did not match the exponential curve, often had the greatest mismatch at the latter times of data sampling. Such later samplings typically contributed more heavily to the end results. Hence, an error at the later points of the concentration curve accentuated the curve fit error. Patients with impaired lungs, such as heavy smokers, had a particularly bad fit to an exponential or double exponential curve in the latter sampled regions.

The present invention contemplates a new and improved technique for accurately determining the flow, partition coefficient, and the fit or confidence values from CT or other imaged data.

SUMMARY OF THE INVENTION

In accordance with the present invention, xenon end-tidal measurements are taken at time displaced intervals. A sloping straight line is fit to the xenon-end tidal measurements taken at intermediate times. Another curve is fit to the earlier xenon-end tidal measurements. In a more limited preferred embodiment, the earlier data is fit to an exponential curve.

In accordance with a more limited aspect of the present invention, the best fit sloping straight line and other curve are integrated to determine xenon blood concentration. The partition coefficient, flow rate, tissue clearance, or build-up rate, and other conventional information are derived from the concentration as is appropriate to the intended application.

In accordance with a more limited aspect of the present invention, a method of determining at least a partition coefficient and flow values corresponding to each of a plurality of voxels of a region of interest is provided. After starting to introduce an enhancement agent into the patient, a concentration of the enhancement agent in a preselected patient tissue, e.g. blood, is measured at intervals over a period of time. An absorption curve characteristic including a saturation value, slope of a linear region, and characteristics of another curve segment are projected. Also, after starting to introduce the enhancement agent into the patient, a plurality of image representations are generated. Each image representation is defined by a plurality of pixels which correspond to voxels of the region of interest. Each image representation includes a pixel value for each pixel. This pixel value is indicative of the enhancement agent concentration in the corresponding voxel at the corresponding time. The at least one of the partition coefficients and flow values are calculated from the absorption curve characteristics and the variation of pixel values with xenon inhalation time.

In accordance with another aspect of the present invention, an apparatus is provided for creating images representing partition coefficient and blood flow rates in a region of interest. An enhancement agent means introduces an enhancement agent into a patient's blood. A concentration measuring means provides an indication of the concentration of the enhancement agent in the patient's blood. An absorption curve segment projecting means projects at least three absorption curve segments that are indicative of enhancement agent absorption by the blood. An imaging means generates a plurality of time displaced electronic image representations of the region of interest. Each image representation includes a plurality of pixel values that are indicative of enhancement agent concentration in corresponding subregions of the region of interest. A partition coefficient and blood flow rate means determines partition coefficients and blood flow rates from the pixel values and the projected absorption curve segments.

A primary advantage of the present invention is that it generates flow and partition coefficient values accurately, even in lung function impaired patients.

Another advantage of the present invention is that it generates flow, partition coefficient, and confidence images quickly, as well as more effectively.

Yet another advantage of the present invention is that it determines partition coefficient and blood flow values of smokers and other patients with fogged lungs accurately and quickly.

Still further advantages of the present invention will become apparent to those of ordinary skill in the art upon reading and understanding the following detailed description of the preferred embodiment.

BRIEF DESCRIPTION OF THE DRAWINGS

The invention may take form in various steps and arrangements of steps and in various components and arrangements of components. The drawings are only for purposes of illustrating a preferred embodiment and are not to be construed as limiting it.

DETAILED DESCRIPTION OF THE PREFERRED EMBODIMENT

Figure 1A:
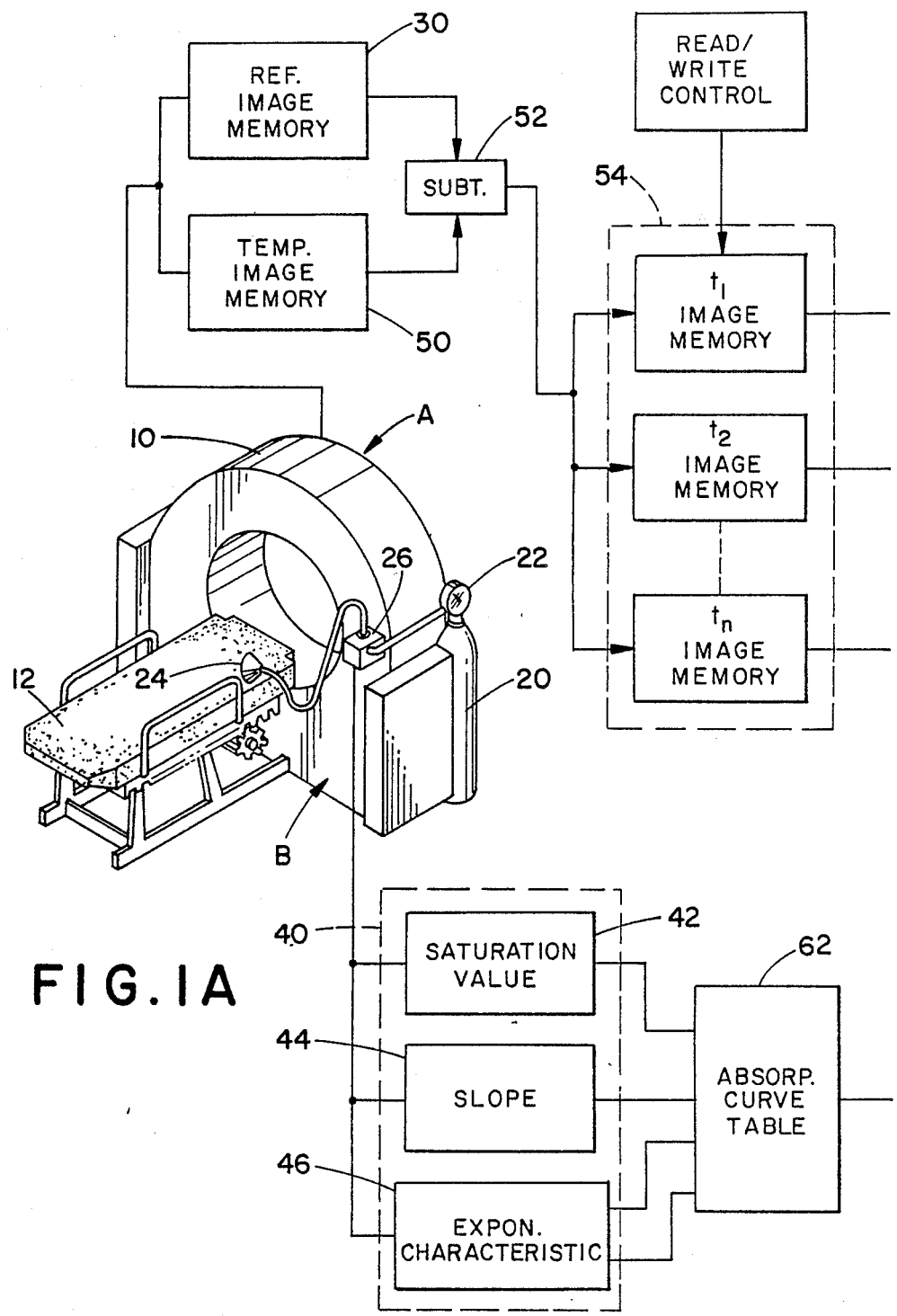
FIGS. 1A and 1B are two parts of a diagrammatic illustration of an imaging apparatus in accordance with the present invention.
Figure 1B:
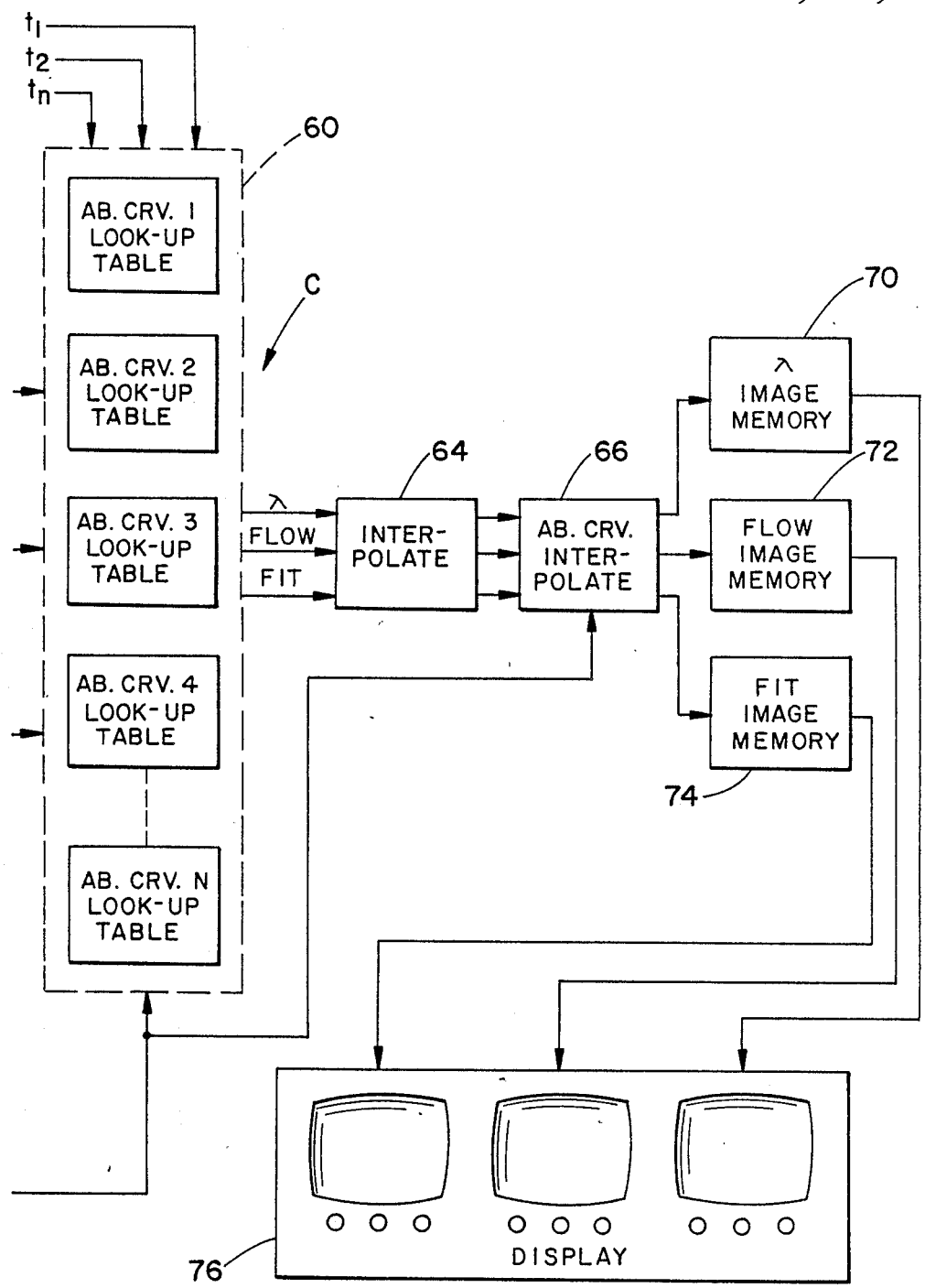

With reference to FIGS. 1A and 1B, an imaging means A, such as an axial tomographic scanner, selectively examines a subject and reconstructs image representations depicting properties of each voxel or subregion within an examined region of interest. An enhancement agent system B introduces selected amounts of an enhancement agent into the subject and derives an indication of the enhancement agent concentration in at least selected portions of the subject. The enhancement agent is selected such that its concentration or presence in the subject alters the image representations. In the preferred embodiment, the enhancement agent is xenon gas whose concentration is reflected in the CT numbers of the reconstructed image representations. That is, the resultant image representations are essentially the sum of two images - an image depicting the xenon gas in voxels of the region of interest and an image of the tissue in the region of interest. A processing means C processes the image data from the CT scanner A collected with varying concentrations of the enhancement agent and processes enhancement agent concentrations from the enhancement agent system B to derive images representing partition coefficient or permeability, blood or other fluid flow rates, and a confidence value or degree of fit.

In the preferred embodiment, the imaging means A is a CT scanner, although a digital x-ray scanner, a magnetic resonance imager, or other diagnostic scanning device may be incorporated. In the CT scanner embodiment, the scanner includes a gantry 10 which houses a rotating x-ray source and radiation detectors. Images from a CT scanner are indicative of x-ray absorption/transmission properties of tissue in each voxel of one or more planar regions of interest or slices. In a magnetic resonance scanner, the gantry houses appropriate electromagnetic coils and antennae. A patient supporting couch 12 selectively indexes the subject through the gantry such that one or more planar slices are selectively imaged.

The enhancement agent system B includes a source 20 of enhancement agent, such as a tank of oxygen and xenon gas. A flow or pressure regulator 22 controls the supply rate of the xenon gas to a breathing mask 24 or other means for introducing the enhancement agent into the patient. An enhancement agent concentration means 26 determines concentrations of the enhancement agent within the patient. More specifically, the concentration agent determining means determines xenon concentration in end-tidal gases expelled from the patient's lungs. The xenon concentration in the end-tidal gas, i.e. the last bits of gas expelled from the alveoles, is in substantial xenon equilibrium with the patient blood.

During a study, the end-tidal concentration values increase with each breathing cycle until a saturation level is attained. Before the xenon gas or other enhancement agent is introduced to the patient, a reference scan is conducted to generate an image representation depicting the imaged region of the enhancement agent. The reference image is stored in a reference image memory 30. Upon completion of the reference image at a time $t_0$, the enhancement agent system B starts supplying xenon gas to the patient. For example, xenon may be substituted for 30% of the gases breathed by the patient. At the end of each respiratory cycle, generally every few seconds, the breath analyzer means 26 determines the concentration of xenon in the patient's blood, more specifically in the end-tidal gases each time the patient exhales.

Figure 2:
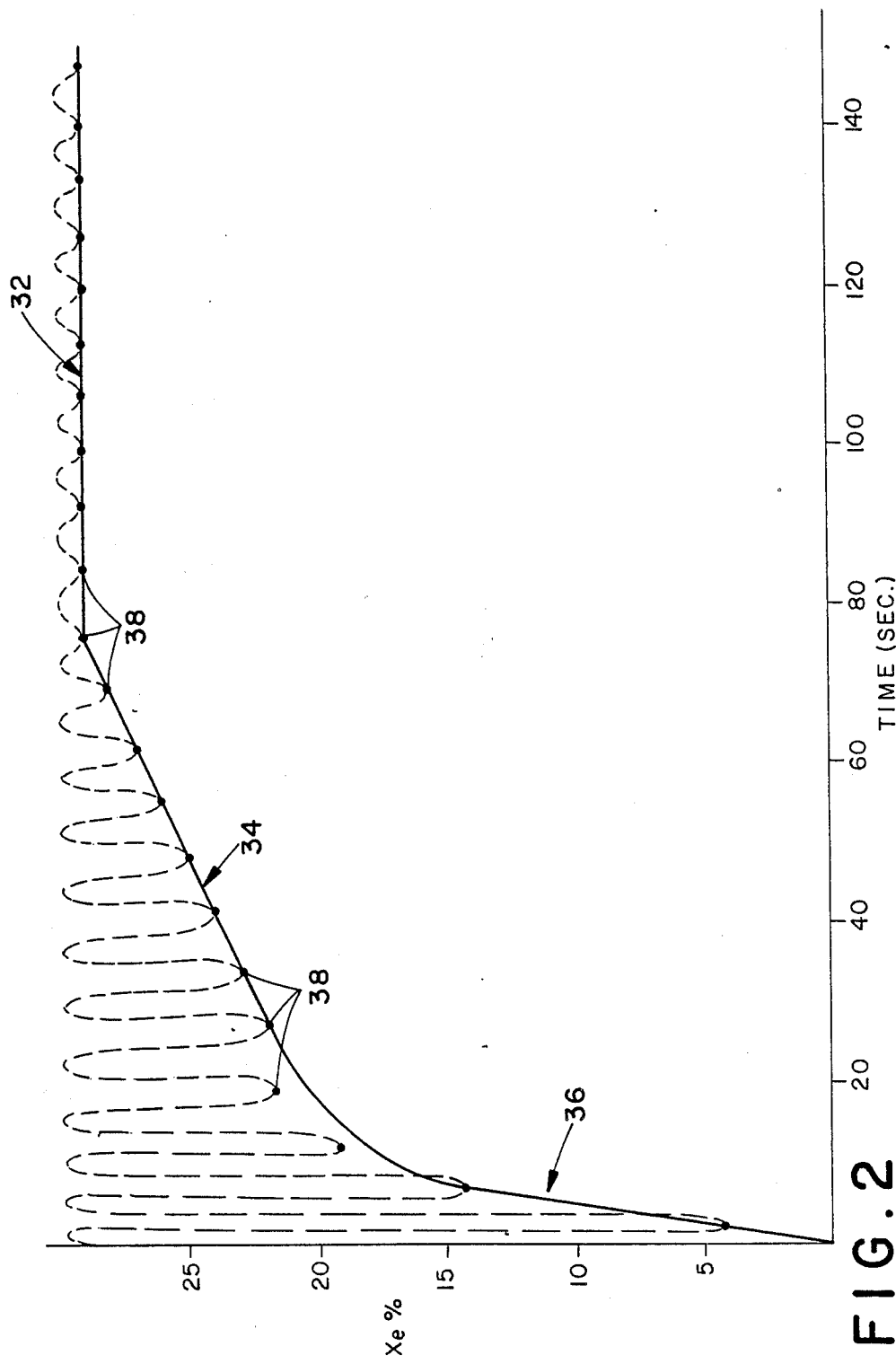
FIG. 2 is illustrative of patient blood absorption curve fitting techniques in accordance with the present invention.

With reference to FIG. 2, the increase in xenon concentration in the blood increases with time. More specifically, the concentration approaches a saturation level 32 with a linear region 34. When xenon is first introduced into the breathing gases, the concentration in the blood builds rapidly and can be approximated as an exponential or other known curve, e.g. a straight line. However, because the concentrations collected later approaching saturation tend to be weighted more heavily in the mathematical processes described herein below, it is often more important to match the second curve portion 34 than the first curve portion 36. The exhalation analyzer monitors xenon concentration which cyclically varies with each respiratory cycle. The end-tidal concentrations 38 that are indicative of blood xenon concentration increases with each respiratory cycle.

A first curve fitting means 40 utilizes standard curve fitting techniques to determine three or more "best fit" curve segments to the end-tidal concentrations. The curve fitting means 40, of the preferred embodiment, performs a four-fold parameterization to determine (i) the final or saturation value, (ii) the fraction of the final value that marks the interface between the first curve 36 and the linear region 34 and (iii) the slope of the later time curve 34. For an exponential first curve, it further determines (iv) the characteristic time constant. More specifically, the curve projecting means 40 includes a saturation value determining means 42 which determines the amplitude characteristic of the last curve 32. A slope determining means 44 determines the slope of the linear curve segment 34. A first curve characteristic determining means 46 determines the characteristics of the first curve 36. For an exponential first curve, the first curve characteristic determining means 46 determines the end point of the exponential curve, i.e. the interface between curves 34 and 36, as well as the time constant of the exponential. Of course, the blood xenon absorption curve may be divided into more than three parts, e.g. four or more parts. Additional corresponding curve segment characteristic determining means may then determine the characteristics of the additional curve portions, such as slope, interface points between the curves, exponential time constants, or the like. The characteristics are selected in accordance with the family curves to which the actual data is fit. For three curve segments, four characteristics are generally defined— one to describe a characteristic of each segment and one to relate the central segment to the other two. As the number of segments among which the blood xenon absorption curve is divided becomes larger, approximating the curve by linear segments tends to approximate the actual absorption more accurately.

As the xenon concentration in the patient's blood is building, a plurality of images of the planar region are generated at preselected sampling intervals or times $t_1$, $t_2, \ldots t_n$. The CT image sampling intervals need not coincide with the sampling intervals of the blood xenon concentration determining means 26. As each image is reconstructed, it is stored temporarily in a temporary memory means 50. A substraction means 52 subtracts each image from the reference image in reference image memory 30 to produce a difference or xenon concentration image which is representative of xenon concentration. A difference image memory means 54 stores a plurality of difference images, each corresponding to a different sampling interval or time, $t_1, t_2, \ldots t_n$. In the preferred embodiment, the first sampling interval $t_1$ is one and a half minutes after $t_0$, the second sampling interval is three minutes after $t_0$, and a third sampling interval $t_3$ is five minutes after $t_0$. Optionally, a fourth sampling interval at $t_4$ may be taken 7 minutes after $t_0$.

Each difference image is defined by an array of pixels, each pixel corresponding to a voxel or subregion of the region of interest but at different sampling times or intervals. The concentration of xenon in the corresponding tissue voxel or pixel can be expected to increase generally logarithmically with time. The partition coefficient, $\lambda$, the blood flow, the fit or confidence values, and other characteristics can be calculated from this logarithmic tissue xenon absorption curve and the blood xenon absorption curve. The blood xenon absorption curve is predicted from the four parameters determined by the absorption curve projecting means 40.

Rather than solving Equation (1), the Kety equation, or otherwise calculating the partition coefficient, flow, confidence, and other values directly, these values are precalculated and stored in a look-up table means 60. The look-up table means may be envisioned as a multi-dimensional look-up table in which each memory element stores a predetermined blood flow value and partition coefficient. The memory is addressed by the four characteristics determined by the blood xenon absorption curve determining means 40 and by a tissue xenon concentration values from the CT image memory means 54. More specific to the preferred embodiment, the look-up table means 60 is addressed by the saturation value, the fraction of the saturation value due to the first or exponential curve portion, the time constant of the exponential, and the slope of the straight line curve portion as determined by the blood xenon absorption curve determining means 40 and by the n corresponding pixel values for the n images stored in the image memory means 54. Because the n images are taken at preselected intervals, the pixel values from these memories serve as a multi-parameter indication of the logarithmic tissue absorption curve.

In the preferred embodiment, the look-up table includes a finite, preselected number of values for each of the addressable parameters. Because in theory the blood absorption curve determining means could project a substantially infinite number of values for each of its four or other number of characteristics, the characteristic values which it may select is limited. Specifically, an absorption curve look-up table selection means 62 adjusts the values of the blood xenon absorption curve characteristics to preselected values or look-up table addresses. Because the CT numbers stored in the image memory 54 are conventionally digital values, only a finite number of values of these parameters are provided. If it is desirable to reduce the size of the look-up table means 60, the number of bits which are utilized to address the look-up table means may be reduced. Alternately, a tissue xenon concentration curve fitting means may fit the CT numbers or pixel values corresponding to each voxel of the region of interest to a best fit one of a family of generally logarithmic tissue xenon absorption curves.

In a preferred method for loading the look-up table means, partition coefficients, blood flow rates, and absorption curves are selected which span the range normally encountered in human patients. The number of partition coefficients, blood flow rates, and absorption curves selected determines the precision with which the final answer is reached but increases the size of the multi-dimensional look-up table and the complexity of the calculations to fill it. For a given blood flow rate, partition coefficient, and blood absorption curve, the tissue xenon concentration curves are calculated from the Kety equation. The calculated xenon concentration curves give the exact concentration at each of the preselected sampling intervals or times $t_1$, $t_2$, $t_3$, etc., i.e. the concentration or pixel values which address each stored blood flow value and partition coefficient. Because all possible concentrations which might be measured at $t_1$, $t_2$, $t_3$, etc. will not fall exactly on a theoretically calculated xenon curve, many of the look-up table entries will remain unfilled. To fill these remaining look-up table entries, the CT number values theoretically predicted at each sampling time are varied randomly by a small amount. These statistic variations generate additional look-up table entries with varying likelihoods. The most likely flow and $\lambda$ values are then used to fill the remaining memory cells. Because these are predicted on a statistical basis, each only has a degree of likelihood or confidence, which is then also stored in the memory cell along with the chosen flow and $\lambda$ values.

In the preferred organization, the look-up table means 60 is actually a plurality of look-up tables. Each look-up table corresponds to one of a plurality of preselected blood xenon absorption curves, $C_a(w)$ of Equation (1) and xenon sampling intervals, $t_1$, $t_2$, $t_3$. The absorption means 62 selects the closest look up tables based on the four characteristics. Each of the closest look up tables are addressed by the outputs of the image memory means 54. If different sampling times, $t_1$, $t_2$, $t_3$ may be selected, an additional sets of look-tables is provided for each array of sampling times. The selected look-up table is addressed by the three or more CT numbers generated from the CT image memories 54.

If the CT numbers or pixel values of the image memories 54 are determined with a higher resolution than the addresses of the look-up table, then the two closest precalculated values for each image are addressed. An interpolating means 64 interpolates among the multiple retrieved partition coefficient, blood flow, and confidence values, preferably in accordance with the relative degree of closeness of the actual value to the preassigned matrix value for each of the images. That is, a weighted averaging of the 2n addressed values, for 2n images, is performed by the interpolation means 64.

As indicated above, the actual characteristics or parameter values determined by the blood absorption curve determining means in many instances will not exactly match any one look-up table. Look up tables corresponding to twice the number of parameters utilized to project the blood xenon absorption curve may be addressed. A second interpolation means 66 performs a weighted averaging of the partition coefficient, flow, and confidence values interpolated by the first interpolating means 64 for each of these look-up tables. If the sampling times $t_1$, $t_2$, $t_3$, ... $t_n$ may also be varied, a third interpolating means may be provided to interpolate relative to these parameters.

A partition coefficient memory means 70 stores partition coefficient values corresponding to each pixel of the CT images. Analogously, a flow image memory means 72 stores the corresponding flow value for each pixel and a confidence or fit memory means 74 stores the confidence value corresponding to each CT image pixel. A display means 76 selectively displays the partition coefficient, flow, or confidence images.

The invention has been described with reference to the preferred embodiment. Obviously, modifications and alterations will occur to others upon reading and understanding the preceding specification. It is intended that the invention be construed as including all such alterations and modifications insofar as they come within the scope of appended claims or the equivalents thereof.

Having thus described the preferred embodiment, the invention is now claimed to be:

1. An apparatus for creating images representing partition coefficient and blood flow rates in a region of interest of a subject, the apparatus comprising:
   an enhancement agent means for introducing an enhancement agent into a subject's blood;
   a means for providing an indication of the concentration of the enhancement agent within the blood over time;
   an absorption curve projecting means for projecting an absorption curve indicative of enhancement agent absorption in the blood over time;
   an imaging means for generating a plurality of time displaced electronic image representations of at least the region of interest, each image representation including a plurality of pixel values, each pixel value being indicative of enhancement agent concentration in a corresponding subregion of the region of interest;
   a partition coefficient and blood flow rate determining means for determining partition coefficients and blood flow rates from the pixel values and the projected absorption curve for subregions of the region of interest corresponding to the pixel values;
   a means for assembling the detemined partition coefficients and blood flow rates into images representing partition coefficient and blood flow rates in the region of interest.

2. An apparatus for creating images representing partition coefficient and blood flow rates in a region of interest of a patient, the apparatus comprising:
   an enhancement agent means for introducing an enhancement agent into a patient's blood;
   a means for providing an indication of the concentration of the enhancement agent within the blood over time;
   an absorption curve segment projecting means for projecting at least three absorption curve segments indicative of enhancement agent absorption by the blood during early, middle, and later time periods;
   an imaging means for generating a plurality of time displaced electronic image representations of at least the region of interest, each image representation including a plurality of pixel values, each pixel value being indicative of enhancement agent concentration in a corresponding subregion of interest;
   a partition coefficient and blood flow rate determining means for determining partition coefficients and blood flow rates from the pixel values and the projected absorption curve segments for subregions of the region of interest corresponding to the pixel values;

a means for assembling the determined partition coefficients and blood flow rates into images representing partition coefficient and blood flow rates in the region of interest.

3. The apparatus as set forth in claim 2 wherein the enhancement agent means includes a supply of xenon gas connected with a breathing mask such that the patient breathes xenon with its breathing gases.

4. The apparatus as set forth in claim 2 wherein the at least three absorption curve segments include a saturation line segment, a linear segment, and a third segment and the absorption curve segment projecting means includes means for projecting an amplitude of the saturation line segment, means for projecting a slope of the linear segment, and means for projecting at least one characteristic of the third segment.

5. The apparatus as set forth in claim 4 wherein the partition coefficient and blood flow rate determining means includes a look-up table means which is addressed by the amplitude, slope, and third curve segment characteristic determined by the absorption curve segment projecting means and by the corresponding pixel values of the image representations.

6. The apparatus as set forth in claim 5 wherein the look-up table means is addressable only by discrete values and further including an interpolating means for interpolating partition coefficient and blood flow rates obtained by addressing the look-up table means with the nearest discrete values for the curve segment characteristics and the pixel values.

7. The apparatus as set forth in claim 5 further including:
a partition coefficient memory means for storing a partition coefficient value corresponding to each pixel of the images;
a flow image memory means for storing a flow value corresponding to each pixel; and,
a display means for selectively displaying the stored partition coefficient and flow values as partition coefficient and flow images.

8. A method of determining at least one of partition coefficient and flow values for each of a plurality of voxels of a region of interest of a subject, the method comprising:
at a commencement time, starting introduction of an enhancement agent into the subject;
at a plurality of sampling times, measuring a concentration of the enhancement agent in a fluid of the subject;
determining a saturation value from the measured enhancement agent concentrations;
calculating a characteristic of a best fit first curve segment between the commencement time and a first time before the saturation value is reached;
determining a slope of a best fit second curve segment between the first curve segment and the saturation value;
generating a plurality of image representations each at a selected sampling interval subsequent to the commencement time, each image representation being defined by a plurality of pixels corresponding to voxels of the region of interest and including a pixel value for each pixel, which pixel value being indicative of an enhancement agent concentration in the corresponding voxel;
determining at least a selected one of the partition coefficient and flow values from the pixel values, the saturation value, the characteristic of the best fit first curve segment, and the slope.

9. The method as set forth in claim 8 wherein the step of determining at least the selected one of the partition coefficient and flow values includes:
accessing a look-up table array with the pixel values of corresponding pixels of the image representations, the saturation value, the first curve segment characteristic, and the slope.

10. The method as set forth in claim 9 further including prior to the commencement time:
calculating partition coefficient and flow values corresponding to absorption curves described by preselected saturation, first curve segment characteristic, and slope, an interval between CT images, and preselected pixel values in accordance with a Kety equation;
storing the calculated partition coefficient and flow values in the look-up table array; and,
defining at least preselected saturation addresses, first curve segment characteristic addresses, and slope addresses, and pixel value addresses to access the look up table array.

11. The method as set forth in claim 10 further including interpolating partition and flow values by accessing the look-up table array with the closest addresses to the actually measured saturation value, first curve characteristic, slope, and pixel values.

12. The method as set forth in claim 9 wherein the look-up table array includes a plurality of look-up tables, each look-up table corresponding to a preselected absorption curve and being addressable by the pixel values generated at the selected sampling intervals, the method further including:
selecting a look-up table whose corresponding absorption curve corresponds most closely to the determined saturation value, first curve segment characteristic, and slope.

13. The method as set forth in claim 8 wherein the first curve segment is an exponential curve segment which is described by an end point and a time constant and wherein the first curve segment characteristic determining step includes determining the end point and the time constant.

14. The method as set forth in claim 8 further including displaying man-readable images of the partition coefficients and flow values corresponding to each pixel of the image representations.

15. The method as set forth in claim 8 wherein the step of introducing an enhancement agent into a subject includes administering xenon gas in breathing gases of a human subject.

16. The method as set forth in claim 8 wherein the image representation generating step includes radiographically examining the subject.

17. A method of determining partition coefficient and flow values for each of a plurality of voxels of a region of interest of a patient, the method comprising:
(a) reconstructing a reference CT image representation;
(b) introducing xenon into air breathed by the patient;
(c) repeatedly measuring blood xenon concentrations in the patient, which blood xenon concentrations tend to increase with time;

(d) determining characteristics of at least three absorption curve segments defined by data points from the measured blood xenon concentrations;
(e) generating a plurality of CT image representations each at a selected sampling interval subsequent to the reference image;
(f) substracting each of said plurality of image representations from the reference image to generate a plurality of difference image representations, each of the plurality of difference image representations being defined by a plurality of pixels corresponding to voxels of the region of interest and including a pixel value for each pixel, which pixel value is indicative of a tissue xenon concentration in the corresponding voxel;
(g) determining at least partition coefficient and blood flow values from the curve segment characteristics and pixel values.

18. The method as set forth in claim 17 wherein the curve segments include at least one non-horizontal linear segment and the determined characteristic of the linear segment includes its slope.

* * * * *